United States Patent [19]
Jang et al.

[11] Patent Number: 5,570,693
[45] Date of Patent: Nov. 5, 1996

[54] METHOD AND APPARATUS FOR ULTRASOUND IMAGING AND ATHERECTOMY

[75] Inventors: Yue-Teh Jang; Axel F. Brisken, both of Fremont, Calif.

[73] Assignee: Cardiovascular Imaging Systems, Inc., Sunnyvale, Calif.

[21] Appl. No.: 356,528

[22] Filed: Dec. 15, 1994

Related U.S. Application Data

[63] Continuation of Ser. No. 956,622, Oct. 5, 1992, Pat. No. 5,383,460.

[51] Int. Cl.$^6$ ............................................. A61B 8/12
[52] U.S. Cl. ............................................. 128/662.06
[58] Field of Search .................. 128/660.03, 662.06, 128/772; 606/159

[56] References Cited

U.S. PATENT DOCUMENTS

| | | | |
|---|---|---|---|
| 3,028,752 | 4/1962 | Bacon | 73/623 |
| 4,669,469 | 6/1987 | Gifford, III et al. | 606/159 |
| 4,700,705 | 10/1987 | Kensey et al. | 606/159 |
| 4,771,774 | 9/1988 | Simpson et al. | 606/171 |
| 4,794,931 | 1/1989 | Yock | 128/660.03 |
| 4,802,487 | 2/1989 | Martin et al. | 128/662.06 |
| 4,821,731 | 4/1989 | Martinelli et al. | 128/662.06 |
| 4,899,757 | 2/1990 | Pope, Jr. et al. | 128/662.06 |
| 4,936,845 | 6/1990 | Stevens | 606/159 |
| 4,957,112 | 9/1990 | Yokoi et al. | 128/662.06 |
| 4,990,134 | 2/1991 | Auth | 604/22 |
| 5,000,185 | 3/1991 | Yock | 128/660.03 |
| 5,054,492 | 10/1991 | Scribner et al. | 128/662.06 |
| 5,099,850 | 3/1992 | Matsui et al. | 128/662.06 |
| 5,105,819 | 4/1992 | Wollschäger et al. | 128/662.06 |
| 5,107,844 | 4/1992 | Kami et al. | 128/662.06 |
| 5,115,814 | 5/1992 | Griffith et al. | 128/662.06 |
| 5,125,410 | 6/1992 | Misono et al. | 128/662.06 |
| 5,131,396 | 7/1992 | Ishiguro et al. | 128/662.03 |
| 5,199,437 | 4/1993 | Langberg | 128/662.06 |
| 5,211,176 | 5/1993 | Ishiguro et al. | 128/662.06 |
| 5,383,460 | 1/1995 | Jang et al. | 128/662.06 |

*Primary Examiner*—Francis Jaworski
*Attorney, Agent, or Firm*—Lyon & Lyon

[57] ABSTRACT

A catheter for ultrasonic imaging has a transducer fixed to a cutter. The transducer is moved longitudinally within an artery while in a fixed radial position. Ultrasonic reflections are received and processed to display a planer or rectangular field of view image area of the artery. Other axial planes of the artery can be imaged by radially turning the transducer to a different angular orientation within the artery and then longitudinally moving the transducer to obtain an image of another planer field of view.

23 Claims, 9 Drawing Sheets

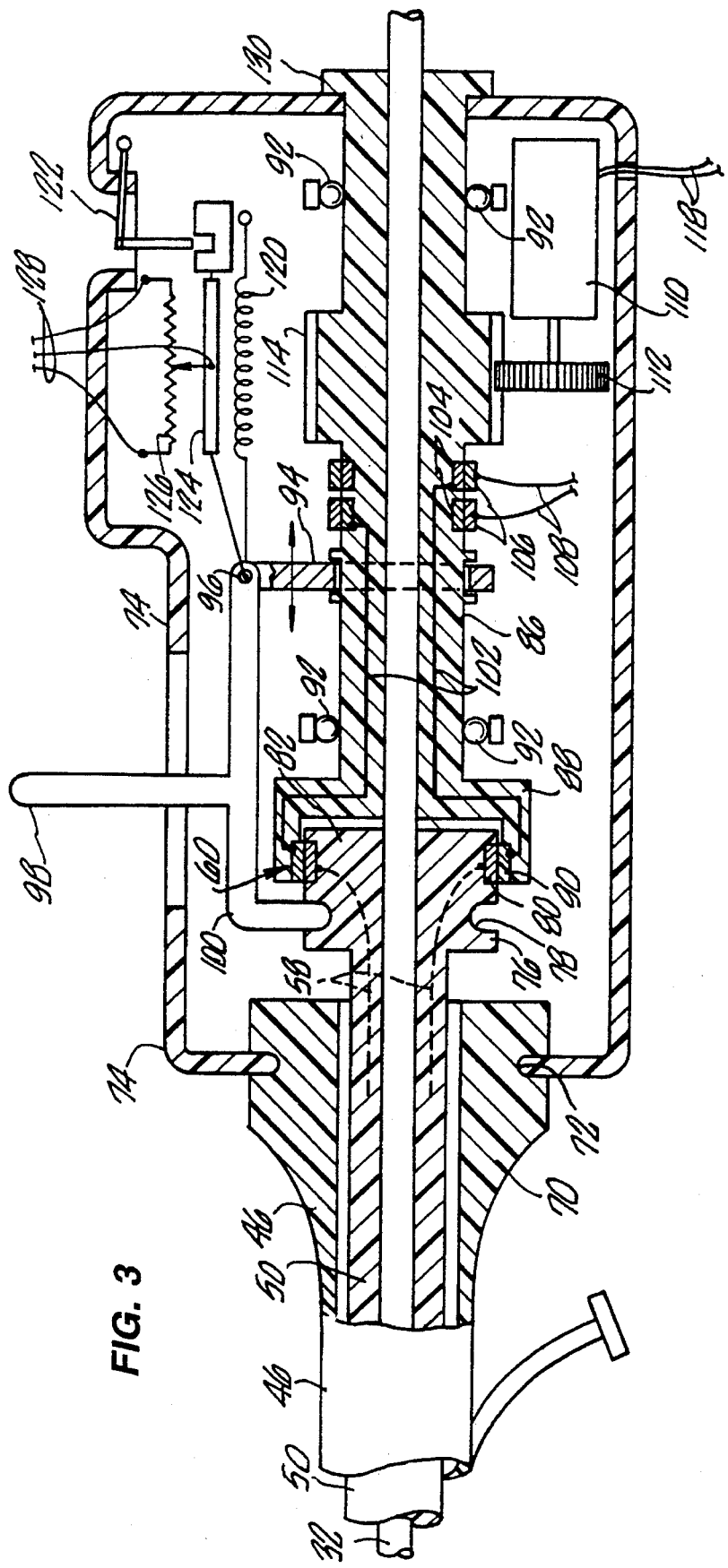

FIG. 3A
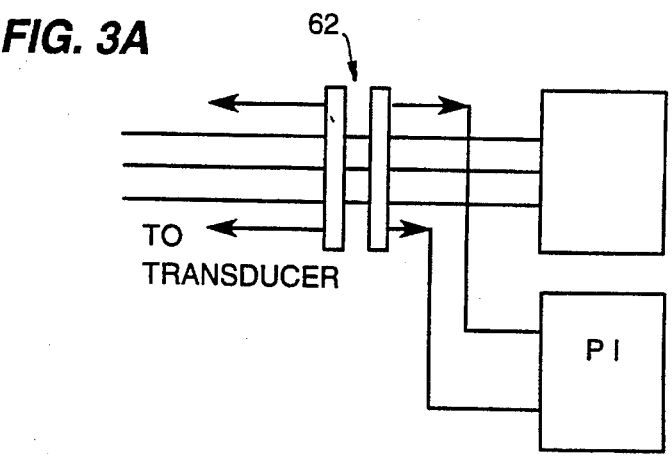
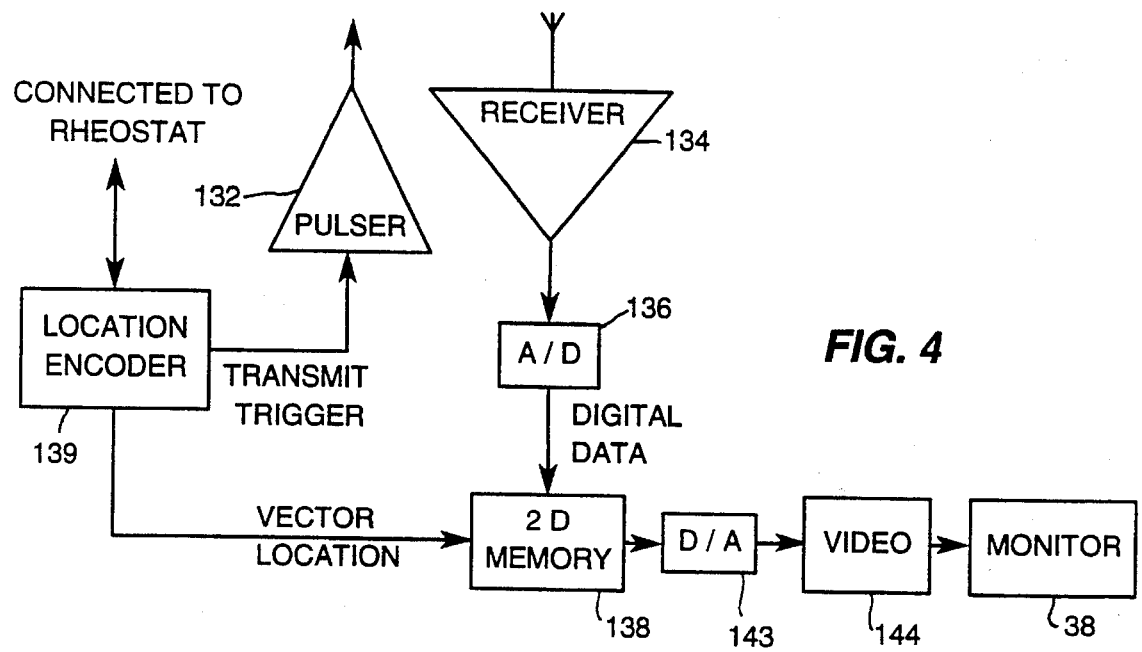
FIG. 4
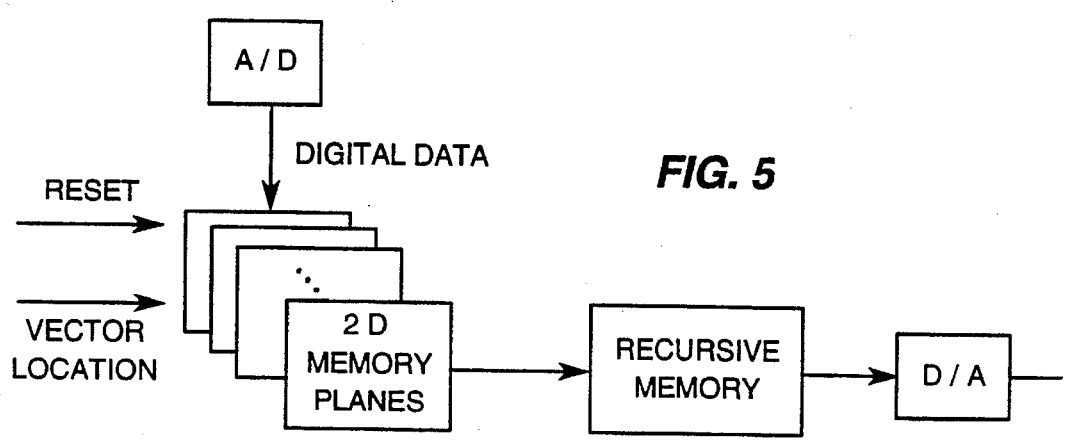
FIG. 5

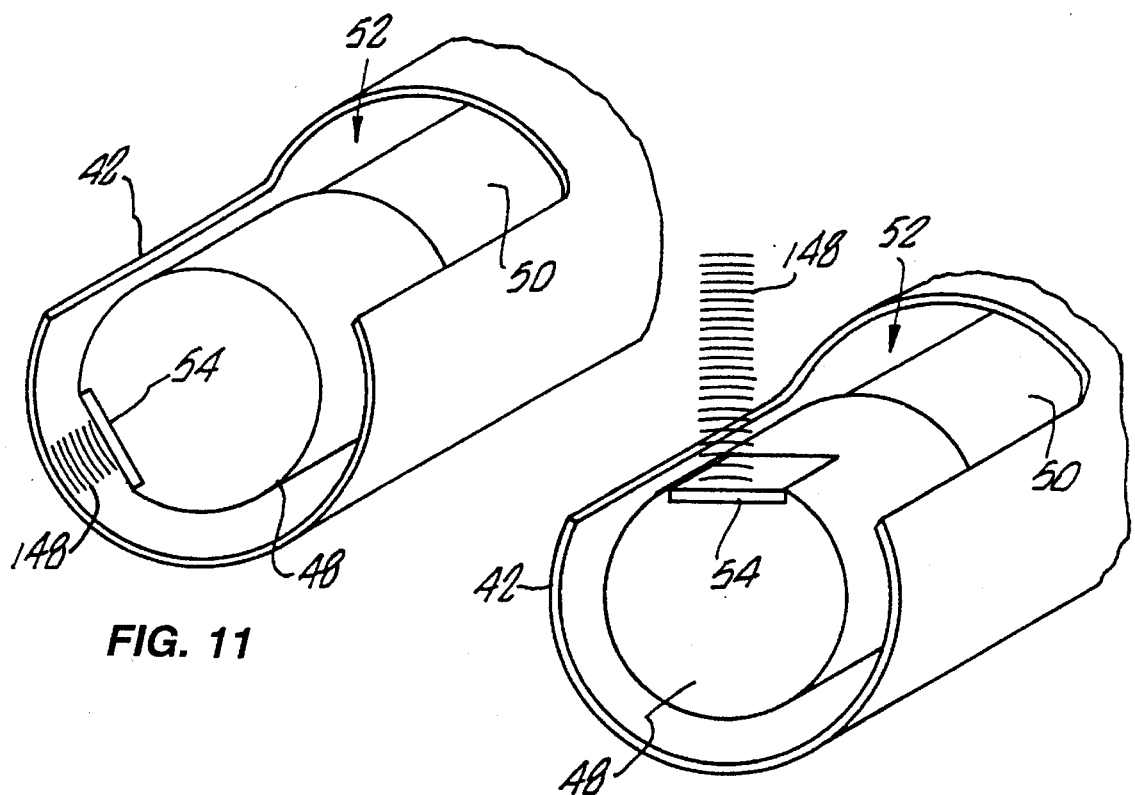
FIG. 11
FIG. 13
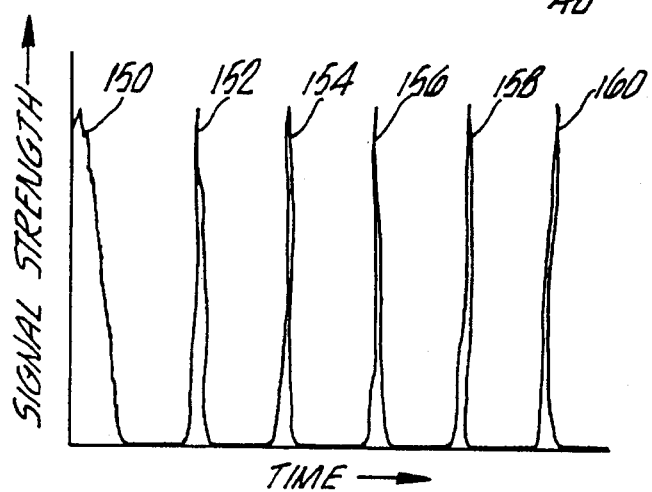
FIG. 12
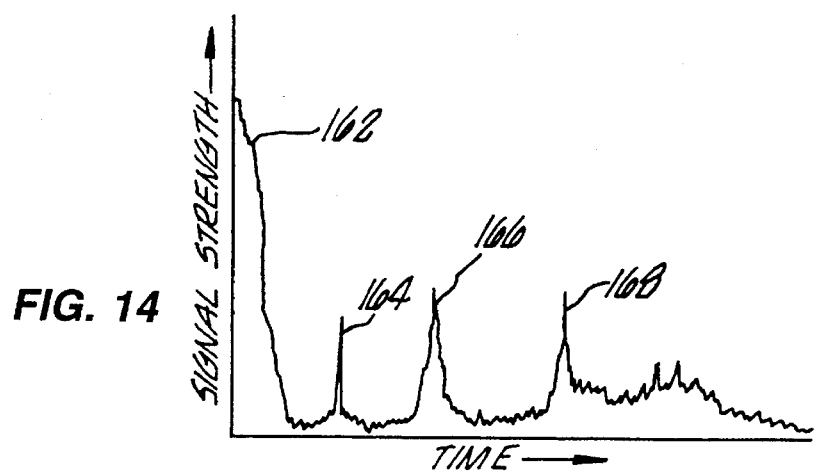
FIG. 14

METHOD AND APPARATUS FOR ULTRASOUND IMAGING AND ATHERECTOMY

This is a continuation of application Ser. No. 07/956,622 filed on Oct. 5, 1992 now U.S. Pat. No. 5,383,460, which is incorporated herein by reference.

BACKGROUND OF THE INVENTION

Various apparatus and methods for intravascular ultrasound imaging and atherectomy have been known and used in the past. Yock, U.S. Pat. No. 5,000,185, describes a method and catheter for performing intravascular two-dimensional ultrasonography and recanalization. Methods of vascular intervention by mechanical cutting have been described in Gifford et al., U.S. Pat. No. 4,669,469, Kensey, U.S. Pat. No. 4,700,705, Pope, U.S. Pat. No. 4,899,757, and Auth, U.S. Pat. No. 4,990,134. In addition, U.S. Pat. No. 4,794,931 further describes a single catheter with combined imaging and cutting capability.

These known apparatus and methods all use a rotating imaging or cutting element at the distal end of a catheter. By rotating the imaging element, for example, a transducer or a transducer/reflector assembly, a real time ultrasound image in the plane perpendicular to the vessel can be obtained. This 360° view of the vessel enables a physician to differentiate tissue structure and fatty deposits in the vessel wall. By moving the entire catheter or the imaging element in the longitudinal direction, a three-dimensional view of the artery can be formed.

SUMMARY OF THE INVENTION

The invention relates to improved apparatus and methods for intravascular ultrasound imaging and atherectomy. An intravascular ultrasound image of a plane parallel to the axis of the vessel or artery is formed by moving an imaging element longitudinally through the artery, rather than radially. Additionally, by rotating the entire catheter, a three-dimensional view of the artery can be formed.

Accordingly, it is an object of the invention to provide an improved apparatus and methods for intravascular ultrasound imaging and atherectomy. Other and further objects and advantages will appear hereinafter.

BRIEF DESCRIPTION OF THE DRAWINGS

In the drawings, wherein similar reference characters denote similar elements throughout the several views:

FIG. 3 is a section view of the proximal end of the present catheter, including the interface to the motor drive unit;

FIG. 3A is a schematic illustration of an inductive coupler;

FIG. 3B is a cross-sectional view of the catheter connector flange which interfaces the catheter to the motor drive unit;

FIG. 4 is a block diagram of the image processing system;

FIG. 4A is a block diagram of an alternative pulser receiver configuration;

FIG. 5 is a graphic illustration of an enhancement to image processing;

FIG. 11 is a schematically illustrated view fragment of the distal end of the catheter, with the transducer facing the housing;

FIG. 12 is a representative example of an A-mode trace associated with the catheter as shown in FIG. 11;

FIG. 13 is a schematically illustrated view fragment of the distal end of the catheter, with the transducer now centrally positioned in the window of the housing;

FIG. 14 is a representative example of an A-mode trace associated with the catheter as shown in FIG. 13;

DETAILED DESCRIPTION OF THE PREFERRED EMBODIMENTS

Figures 1, 2:
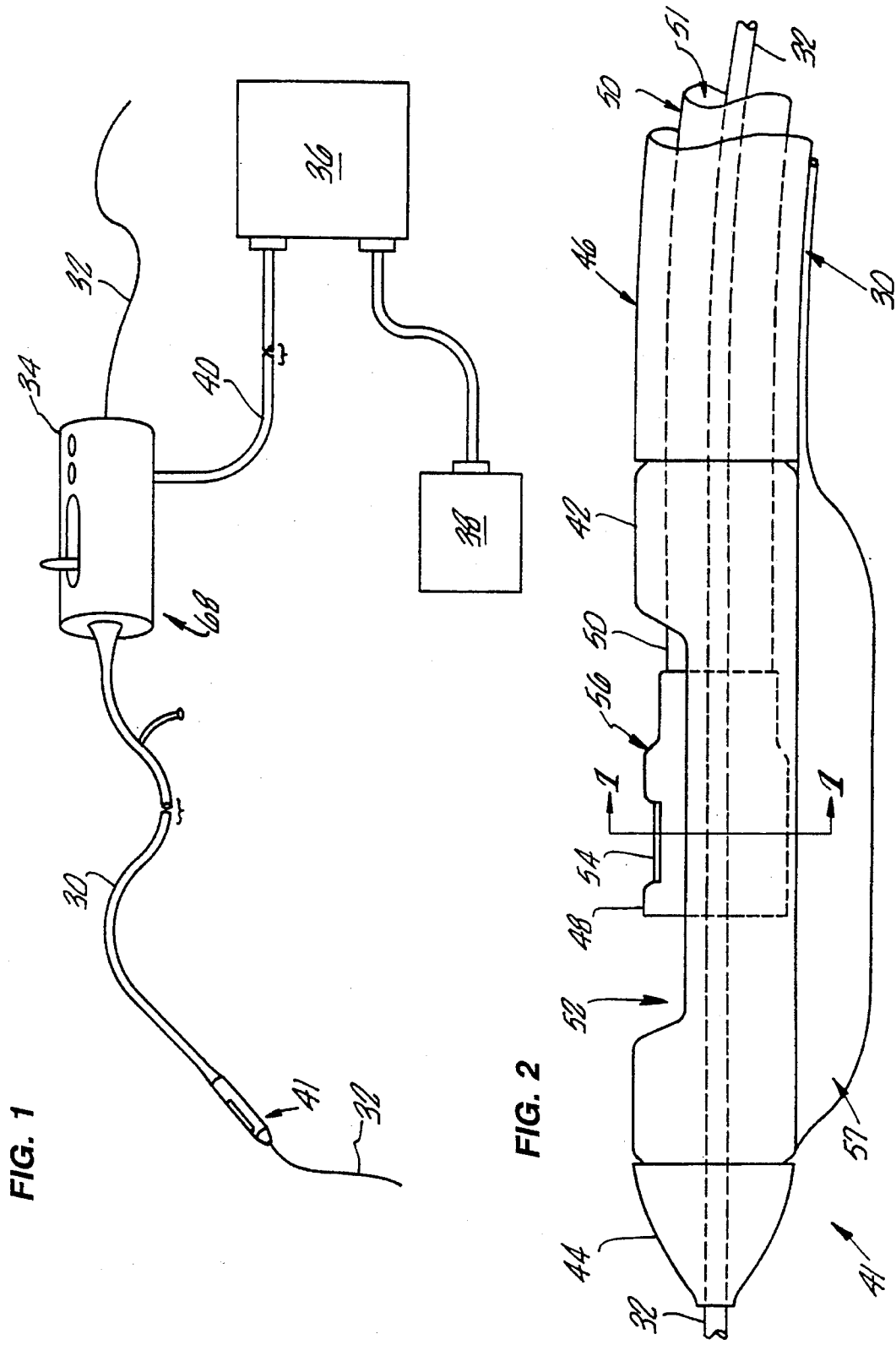
FIG. 1 is a schematic illustration of a preferred embodiment of the present catheter and imaging system.
FIG. 2 is an enlarged side elevation view of the distal end of the present catheter.

As shown in FIG. 1, an apparatus for ultrasound imaging and atherectomy includes a combination imaging/atherectomy catheter 30 operating over a standard interventional guide wire 32, a motor drive 34, a signal processing unit 36, and a video monitor 38. The catheter 30 is intended to operate in vivo in the vascular structure and remains in the sterile field. The guide wire 32 also remains in the sterile field and runs through the center of the catheter 30 and the motor drive unit 34. From one clinical procedure to the next, the motor drive unit is resterilized and is kept in the sterile field during the procedure.

The motor drive 34 is connected with the signal processing unit 36 with a sufficiently long cable 40, allowing the signal processing unit to remain outside the sterile field. Typically, the signal processing unit 36 may be hung from the rail on the catheter lab table, or permanently mounted under the table. Output video signals pass from the signal processing unit 36 to a conveniently located video monitor 38.

FIG. 2 shows the distal end 41 of the present catheter 30, which has a rigid housing 42, a flexible nose section 44 and a flexible shaft 46. A cutter 48 attached to a drive cable 50 is rotatably and axially slidably positioned within the housing 42. The housing 42 has a window or cutout 52. An ultrasonic transducer 54 is attached to the cutter 48 to form a cutter/transducer assembly 56. The transducer 54 can be a PZT crystal or a polyvinylidine fluoride material, or any composite piezoelectric material. As those of ordinary skill in the art recognize, proper backing and an impedance matching layer are applied to the transducer. The exposed surface of the transducer can be flat or concave in shape. A concave transducer surface aids in focusing the ultrasound beam.

The catheter housing 42 is rigid and is advantageously made of metal, for example, stainless steel, to better support the cutter 48 and to provide structural strength for the front end of the catheter 30. The drive cable 50 has a central lumen 51 which also passes through the cutter 48 to allow a guide wire 32 to slidably pass through the drive cable 50 and cutter 48. A balloon 57 is provided at one side of the catheter 30 opposite the window 52. The balloon 57 can be inflated to press the window 52 of the housing 42 against a fatty deposit or plaque, such that cutter 48 can successfully shave material from the vessel wall. More than one balloon may be used, to allow proper positioning of the catheter.

In operation, the catheter 30 is inserted into an artery and positioned in the area of interest. The balloon(s) 57 is inflated to force the window 52 of the housing 42 to move toward the arterial wall and allow fatty deposits to enter the window 52. The inflated balloon(s) also prevents any movement of the housing 42 relative to the artery 29. It is important that the housing 42 be locked in position to obtain proper imaging. Construction details of the catheter 30 are provided in U.S. Pat. No. 5,000,185, the disclosure of which is incorporated herein by reference.

FIG. 3 shows the proximal end of the catheter 30 and its interface with the motor drive unit 34, in cross-sectional view. Transducer lead wires 58 extend back through the catheter 30 around the drive cable 50 to the commutator arrangement 60. The transducer lead wires 58 can also be an integral part of or embedded in the drive cable 50. Inductive couplers, shown at 62 in FIG. 3A, may be used instead of the commutators. The flexible shaft 46 surrounds the flexible drive cable 50 and transducer lead wires 58 which in turn surrounds the guide wire 32.

The motor drive unit 34 is intended to interface with the catheter proximal end 68 to provide rotational movement for the cutter 48, horizontal movement for the cutter 48, electrical read-out of horizontal (longitudinal) position, and electrical connection to the transducer leads 58, with minimal cost in the sterile disposable catheter portions. Specifically to that end, the proximal end 68 of the catheter comprises a rigid connector flange 70 attached to the flexible catheter shaft 46. The housing 74 of the motor drive unit 34 is attached to the flange 70 around an indented groove 72. Additionally, the drive cable 50 has as its proximal end a second rigid connector flange 76 with a retention groove 78 and transducer lead electrical contact plates 80 mounted on the rear portion 82 of the connector flange 76. Rear portion 82 is formed with a non-circular shape, e.g., exhibits an octagonal, rectangular, square or other non-circular cross-section. The wires 58 pass one each to the flat surfaces of the electrical contact plates 80 on the outer surface of the rear portion 82 of the connector flange 76.

Within the motor drive unit 34, a rigid drive shaft 86 with an open central lumen for the guide wire 32 captures the drive cable connector flange 76 with a receptacle 88. As seen in FIG. 3B, receptacle 88 is formed with a non-circular, e.g., octagonal cross-section which mates with a rear portion 82 of the connector flange 76 to prevent relative slippage therebetween as receptacle 88 turns. In this manner, the drive cable 50 rotates with rigid drive shaft 86. Two sets of neighboring internal flat electrical contacts or surfaces 90 make electrical contact with the exposed transducer lead wire electrical contact plates 80 (the shaft 86 and drive cable 50 connector flange 76 turn together).

The rigid motor drive shaft 86 is internally supported by bearings 92 at two locations to allow rotational motion and also horizontal motion, such horizontal motion equivalent to the horizontal travel of the cutter 48 within the housing 42 at the distal end 41 of the catheter 30.

Rotationally anchored to the motor drive shaft 86 is a collar 94 containing a hinge 96 for a combination lever arm 98 and retention clamp 100 for the drive wire connector flange 76. The retention clamp 100 locks into the groove 78 to keep the drive cable connector flange 76 attached to the motor drive shaft 86 while at the same time allowing synchronous rotational motion of both shafts. Horizontal movement of the lever arm 98 causes horizontal movement of the cutter 48 within the housing 42. The operation of the lever arm 98 is further described in U.S. Pat. No. 4,771,774, incorporated herein by reference.

Electrical lead wires 102 imbedded within the motor drive shaft 86 provide a conduction path from the electrical contact points 90 in the flange receptacle 88 to rotational commutator rings 104. The transducer electrical signals pass from the commutator rings 104 and 106 to the signal processing unit 36 via leads 108 and the cable bundle 40.

Rotational movement of the cutter 48 in the housing 42 is provided by electric motor 110, through first and second pinion gears 112, 114. Motor 110 is mounted to the motor drive housing 74. The first pinion gear 112 is attached to the shaft of the motor 110 and drives the second pinion gear 114 which is attached to the rigid drive shaft 86. Gear 114 is longer than gear 112, allowing continuous power train drive during horizontal movement of the drive shaft 86. Electrical leads 118 for motor power pass to the system image processing unit via cable bundle 40. An on-off switch on the motor drive unit 34 permits the user control over rotational motion.

Attached to the lever arm collar 94 is a spring 120 for rapidly and uniformly pulling the lever arm 98 from a maximum distal position to a maximum proximal position. A friction clutch (not shown) on the collar 94 controls pullback speed. A pullback latch 122 can be set and released to initiate automatic pullback.

The motor drive unit 34 includes a linear position encoder consisting of a longitudinal rheostat 124. The wiper 126 or rheostat 124 is attached to the lever arm collar 94. Lead wires 128 from the rheostat 126 and wiper 124 provide horizontal positional feedback to the system signal processing unit 36 via the cable bundle 40. Although shown as a separate unit in FIG. 1, the signal processing unit 36 may preferably be positioned within the motor drive housing.

A motor drive shaft flange or thumb wheel 130 on the proximal end of the motor drive allows manual rotation of the shaft for the purpose of aligning the transducer 54 on the cutter 48 so it is centrally located within the window 52 of the distal housing 42.

Referring to FIG. 4, within the signal processing unit 36 is an ultrasound pulser 132 and a receiver 134 for respectively generating and receiving ultrasound signals from the transducer 54 through commutator 60, commutator rings 104, 106 and associated leads. The receiver 134 is linked to an A/D converter 136 which provides digital data to a two-dimensional memory 138. A location and encoder circuit 139 connected through cable bundle 40 and leads 128 to rheostat 124 reads the output of the rheostat in the motor drive unit and converts the signal to digital bits which correspond to the longitudinal location of the transducer, i.e., which correspond to the column location in the video display of the transducer output. The digital bits indicating longitudinal position (i.e., indicating the video column) are supplied to the two-dimensional memory 138. If a digital encoder, such as a linear optical encoder is used instead of rheostat 124 to determine location, the location encoder circuit 139 would translate the digital encoder code to display memory location code.

Location encoder circuit 139 also supplies a "transmit trigger" pulse to the ultrasound pulser 132. The "transmit trigger" pulse serves as a system clock for the signal processing unit such that ultrasound pulses are generated by the transducer at the proper instant of time. The trigger is also a common electrical reference point to initiate other functions in the signal processing unit associated with receiving the echo stream, setting up and loading the memory, etc.

Alternately, as shown in FIG. 4A, ultrasound pulser 132 may be replaced with a transmit encoder 140 connected to a power pulser 141 located in the motor drive unit 134. Power pulser 141 generates the actual power pulses for the transducer 54. Ultrasound echoes received from the transducer are then processed in a pre-amplifier 142 in the motor drive module 34 before being sent to receiver 134.

Referring back to FIG. 4, the contents of the 2D memory are read by a D/A converter 143 at a rate consistent with video frame rates, passed to a video circuit 144 which translates the 2D image into an NTSC or PAL video standard video signal, and then to conventional display monitor 38. Alternatively, the 2D memory can be read and displayed on a digital monitor in conventional computer formats or displayed on liquid crystal displays by direct line-by-line read-out.

As shown in FIG. 5, the 2D memory may also consist of several memory planes. The displayed image can be recursively averaged as the cutter is moved back and forth, for the purpose of smoothing the image or eliminating noise. A reset pulse from the location encoder 139 tells the memory each time the cutter direction has changed.

The 2D memory is a memory device which is partitioned into rows and columns. There are sufficient columns for as many columns of video pixels on the video display, and there are as many rows as there are horizontal lines on the video display system. The memory is as deep as there are bits per pixel on the display. For every longitudinal position of the cutter in the housing, there corresponds a column in the memory. As the data is received, the A/D converter rate is set such that sampling occurs for every vertical position (pixel) on the display for as many horizontal lines as exist on the display.

Referring to FIGS. 1 and 3, the speed of forward movement of the lever arm 98 is limited by clinical conditions and the user's ability to push it forward, and is typically 5–10 seconds, to allow the cutter 48 to properly cut tissue. The pullback throw is preferably controlled by the spring 120 and pull back latch 122 and should typically not take less than 0.005 seconds to complete, as acoustic data is acquired during this phase. The complete pullback throw should be sufficient to collect all of the acoustic data, but short in time compared to anatomical motion. Alternatively, the pullback throw could be accomplished manually by the user, or acoustic data can be acquired both on forward and backward motion, to continuously update the image during catheter movement.

Images are generated by sweeping the transducer back and forth. Every time the transducer is moved a small amount, the transducer is fired and generates a line of information. If the transducer is moved too slowly, then anatomical motions may affect the image. If the transducer is jerked back quickly, as with a triggered retraction, then all of the acoustic information can be obtained in a time frame small compared to that associated with body movements.

Figure 6:
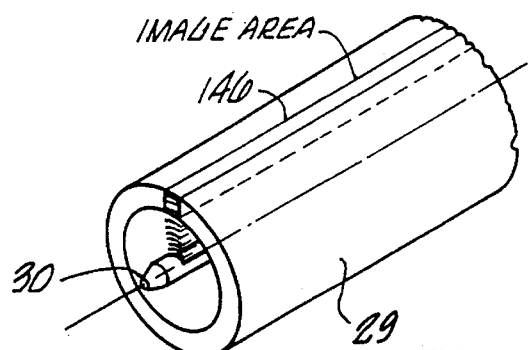
FIG. 6 is a perspective view fragment of the image area provided by the present method and apparatus.
Figure 7:
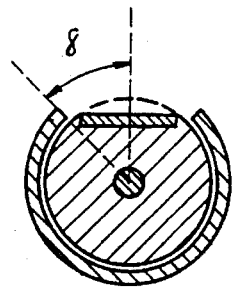
FIG. 7 is a schematically illustrated section view taken along line 7—7 of FIG. 2.
Figure 8:
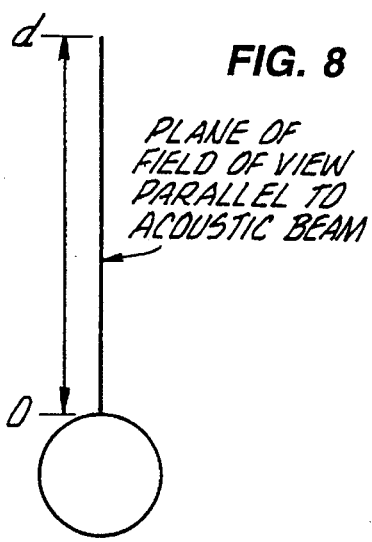
FIG. 8 is a graphic illustration of the plane of field of view.
Figure 9:
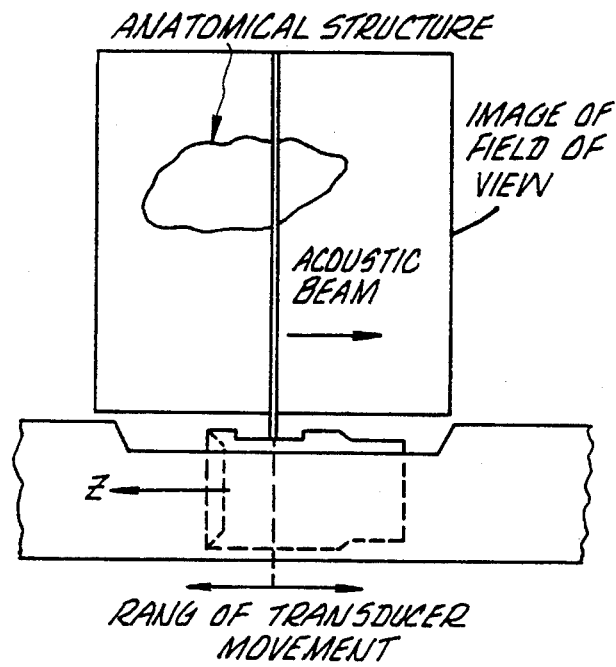
FIG. 9 is a diagram showing transducer movement and the corresponding image formed on the monitor.
Figure 10:
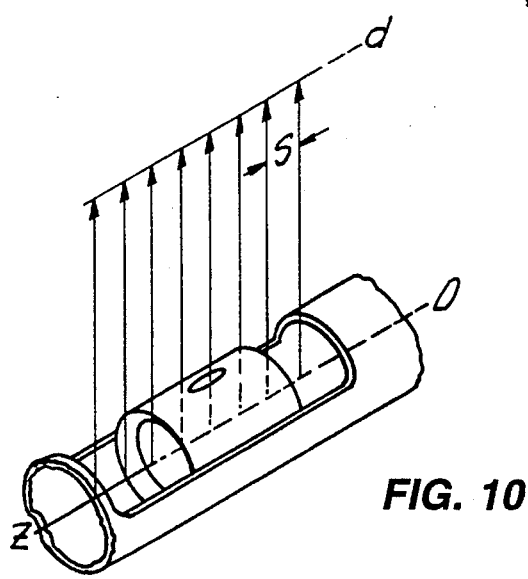
FIG. 10 is a perspective view fragment showing the plane of field of view and the depth "d" of the plane.

FIG. 6 shows the longitudinal area 146 imaged with the present methods. In one method, the cutter 48 carrying the transducer 54 is rotated, while in another method the transducer is not rotated and is maintained in alignment with the window. During imaging, it is important to avoid non-linear movement of the cutter/transducer assembly relative to the artery 29. By inflating the balloon(s) and quickly pulling back the cutter/transducer assembly, especially during the diastolic movement of the heart function, the desired linear movement can be readily achieved.

As shown in FIGS. 7–17, the combined imaging/atherectomy catheter of the present invention is used to acquire images in a longitudinal plane. As can best be seen in FIGS. 7–10, the longitudinal plane extends from the transducer to a chosen depth "d", and along the catheter z-axis for the allowable movement range of the cutter/transducer assembly. In practice, this may be from less than one centimeter to a maximum of about 2 centimeters. Display vectors are parallel to one another and their spacings are determined by circuitry which determines the steps in the z-axis movement. When used with a rotating transducer, an index pulse serves to position the vector in the plane exactly within the window 52. The result of this timing is to define a plane positioned at a predetermined angle θ of the rotating transducer, which is formed by the vectors of depth "d" moving along the z-axis of the catheter/transducer.

An image of the tissue or other anatomical structure of interest which intersect the plane described above is made up of digitized ultrasound data taken from each vector. This data is displayed either with vectors oriented vertically, or with vectors oriented horizontally along the raster of the output device.

As shown in FIG. 11, the transducer 54 on the cutter 48 within the housing 42 of the combined imaging/atherectomy catheter is directed toward the wall of the housing. The imaging ultrasound beam 148 cannot propagate acceptably through the metal of the housing and in fact most of the energy will reverberate between the transducer and the housing wall. FIG. 12 depicts a typical A-mode tracing of the received acoustic waveform, showing the ringdown 150 of the excitation, the first acoustic echo from the housing wall 152, the first reverberation off the housing wall 154, and subsequent reverberations 156, 158, 160 off the housing wall.

If the cutter 48 is rotated by the drive cable 50 and thumbwheel (or the motor) such that the acoustic beam 148 is now centrally positioned in the window of the housing, as shown in FIG. 13, the acoustic beam 148 is then free to propagate through the human tissue and might present with an A-mode trace as shown in FIG. 14, where 162 represents the same excitation ringdown as seen in FIG. 12 (ringdown 150), with low signals 164 due to scatter from blood and enhanced echoes 166 and 168 due perhaps from tissue structures such as the internal and external elastic lamina of the vessel wall.

Figure 15:
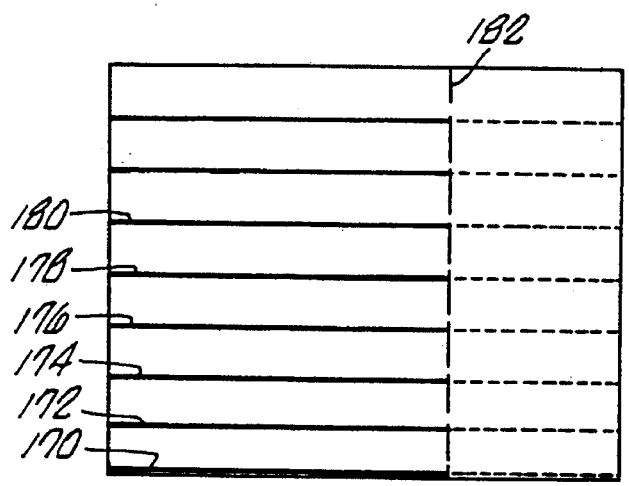
FIG. 15 is a representative example of an image generated upon pulling back the imaging element as shown in FIG. 11.

With the cutter in the position shown in FIG. 11, such that the acoustic beam 146 strikes and reverberates off the housing wall, pullback of the cutter for the purpose of generating an image will result in an image illustrated in FIG. 15, where the horizontal line 170 corresponds to the excitation ringdown 150, the horizontal line 172 to the first echo 152 off the housing wall, horizontal line 174 to the first reverberation 154 off the housing wall, etc. The vertical line 182 corresponds to the current position of the transducer in its pullback through the length of the window, with the dashed lines to the right indicating anticipated images due to the continued reverberation.

Figure 16:
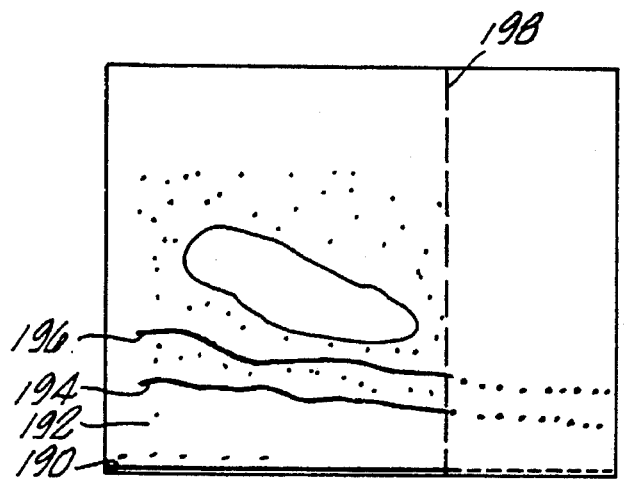
FIG. 16 is a representative example of an image generated upon pulling back the imaging element as shown in FIG. 13.

With the cutter rotated to align the transducer within the window such that the acoustic beam freely passes through the window, one might see an image of the type shown in FIG. 16, where the horizontal line 190 represents the excitation ringdown 162 as in FIG. 14, and the remaining features are identified as the absence of echo 192 corresponding to the blood region with minimal echo 164 as seen in FIG. 14, the internal elastic lamina line 194 and the external elastic lamina line 196 corresponding to echos 166 and 168 of FIG. 14. The vertical line 198 represents the current position of the transducer, with the image to the left representing past history (anatomy just scanned) and the dashed lines to the right representing anticipated images from anatomy to be scanned.

In the preferred embodiment of this invention, with the intent of keeping the hardware and operation simple, the user would adjust the angular orientation of the cutter such that the transducer were positioned midway in the window, by the manual rotation of the thumb wheel at the motor drive assembly. The thumb wheel communicates with the cutter via the drive cable 50, with the drive cable having sufficient torsional rigidity so as to provide one-to-one rotation between the thumb wheel and the cutter. The user would use the acoustic signature on the screen as a means to determine when the cutter has achieved the proper orientation.

Figure 17:
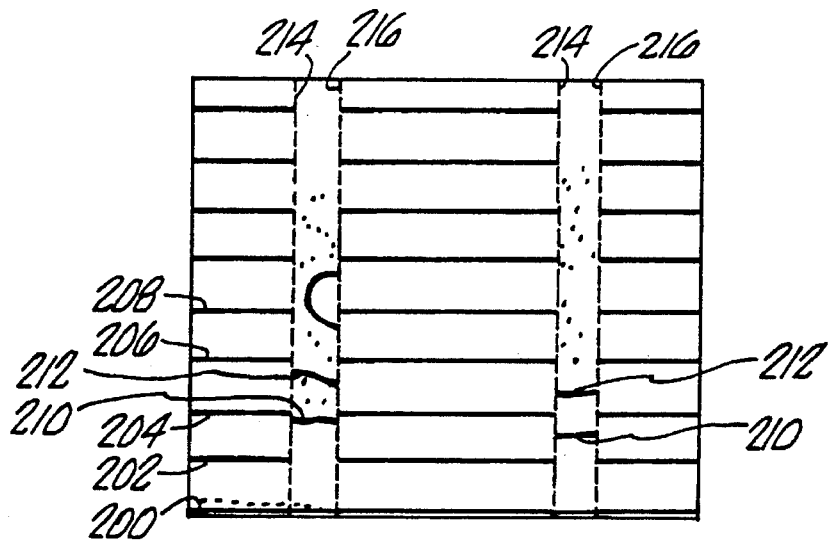
FIG. 17 is a representative example of an image generated upon pulling back the cutter (and transducer) with the transducer electrically active in the pulse echo mode while the cutter (and transducer) are being rotated by the motor drive.

Should the transducer be electrically active in the pulse echo mode while the cutter is being rotated by the motor drive and while a pullback is taking place, one might expect an image as illustrated in FIG. 17. Horizontal trace 200 represents the excitation ringdown of the transducer; horizontal lines 202, 208, 202, 208 represent acoustic images of the housing wall and the first, second and third reverberations, respectively; and generally diagonal lines 210 and 210 represent the internal and external elastic lamina of the vessel, respectively. Vertical lines 214 represent the transition as the acoustic beam passes from a reverberation mode bouncing off the housing wall to free imaging through the window of the housing. Vertical lines 216 represent the subsequent transition, as the cutter continues to rotate and the transducer again faces the housing wall, with the acoustic beam reverberating off the wall.

Figure 18:
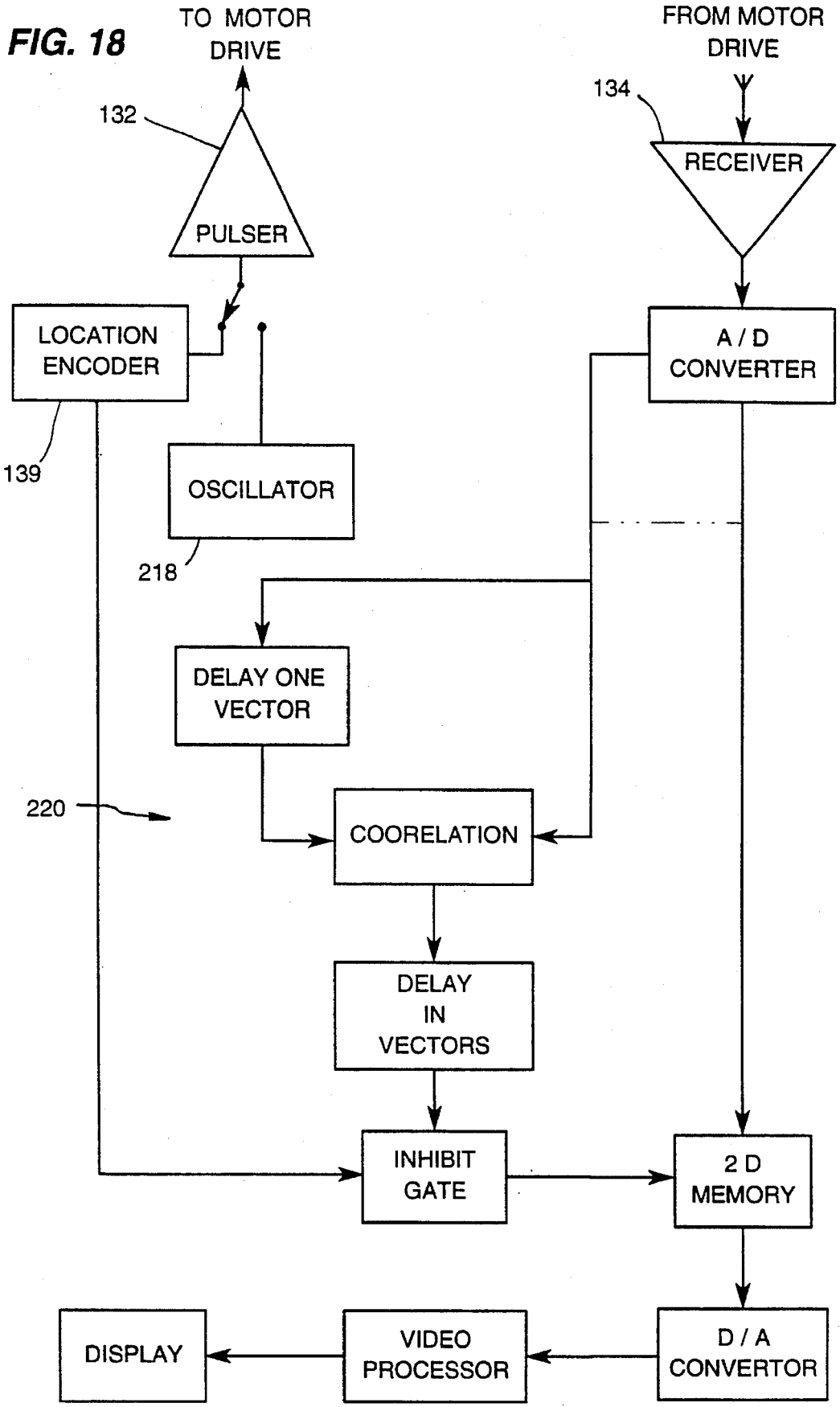
FIG. 18 shows a signal processing circuit for imaging during pullback with the motor unit turning the cutter/transducer assembly.

For imaging the interior vessel wall with the motor turning the cutter assembly, and with simultaneous pullback, the signal processing circuit shown in FIG. 4 is modified, as in FIG. 18. The oscillator 218 in FIG. 18 causes the pulser to fire at a frequent, regular interval. A typical pulse rate is on the order of 30 KHz. The echo pattern is passed back to the signal processor receiver, where the signal is detected and converted to digital form by the A/D converter. The digital signal passes to the 2D memory in the same manner as in FIG. 4.

The detected signal also branches (either before the A/D converter in the analog form, or after the A/D converter in the digital form) to a waveform recognition circuit 220. In this circuit, the waveform passes to a correlator circuit, and is compared to the previous waveform (which is passed to the correlator circuit at the same time, after having been delayed by one vector or pulse rate period). If the two waveforms match, the transducer has seen the wall of the housing twice in a row, and therefore is still at the incorrect orientation for vessel wall imaging. The correlator enables the "Delay N Vector" circuit, in turn setting the "Inhibit Gate" circuit to send an INHIBIT signal, which prevents the location encoder from updating the 2D memory, and consequently prevents received echo data from entering the memory for display. If the correlator does not see a match between two consecutive waveforms, the acoustic beam is either entering the window of the housing, is in the window and seeing different anatomical structures, or is exiting the window. Upon this condition, the INHIBIT signal is deactivated for one transducer pulse period, at a specified time delay after first sensing this condition, with such delay provided to allow the acoustic beam to reach the center of the window. Operation of the waveform recognition circuit 220 is timed from the "transmit trigger" pulse output from the location encoder circuit 139.

Without the INHIBIT signal, the encoder location position is passed to the 2D memory and the received data vector in the digital format is written at the appropriate location in the memory. If pullback is slower than appropriate with respect to the rotation of the cutter, individual data vectors in the 2D memory will be overwritten, without degradation to image quality. If the pullback is too fast, the image will be present with gaps.

The 2D memory might be configured as a dual port RAM. At time frames consistent with scanning, the memory would be loaded, irrespective of display frame rates. At time frames consistent with the video formats, the memory would be read, converted to analog video format, and transmitted to the appropriate video display hardware, in the given video standard.

Another embodiment causes the motor driver to stop rotation as a result of the INHIBIT/NON-INHIBIT transition so as to cause the cutter to be so oriented that the acoustic beam passes through the center of the window, allowing tissue imaging during the entire length of the pullback. In this mode, signal processing would occur as if the cutter had been aligned with the window by the operator.

Figure 19:
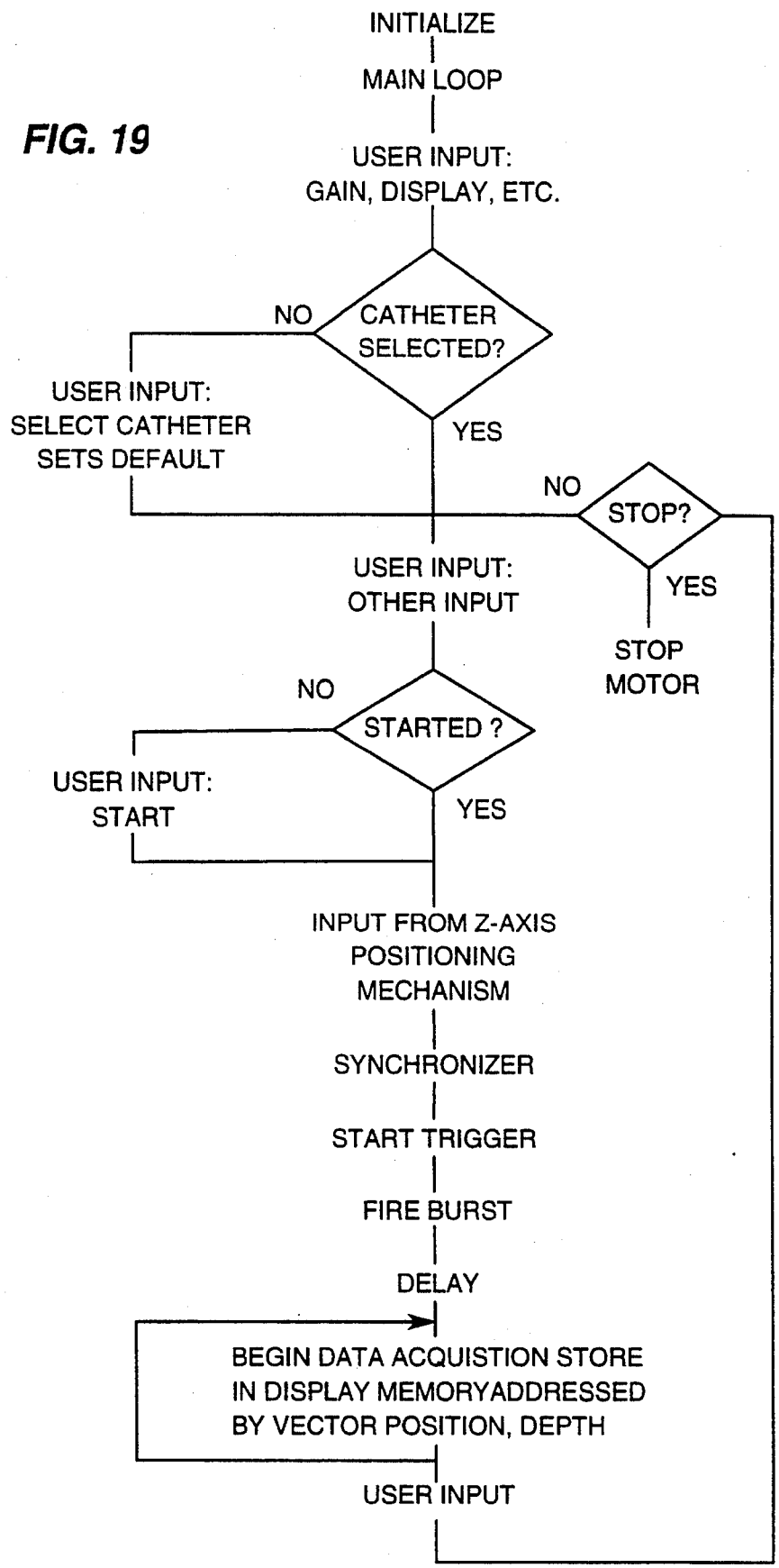
FIG. 19 is a flow chart illustrating a preferred method of algorithm for linear display of catheter images.

FIG. 19 depicts a flow chart outlining the operation of signal processing unit 36. Each vector is generated by a trigger module (not shown) in the location encoder circuit 139 which takes its input from the z-axis movement of the cutter/transducer. The trigger module is responsible for introducing the appropriate time delays associated with the transducer geometry. A positioning mechanism is necessary to keep track of each new vector being updated.

The algorithm used to acquire and display the ultrasound image data is as follows:

1. Initialize at power on.
2. Enter main loop which scans user input and implements the selection. Set gain, TGC, display presentation adjustments.

3. Continue in main loop.
4. Wait for user catheter selection;
   a. set defaults based on frequency, depth, linear scan distance, burst.
   b. paint markers etc. on display,
5. Wait for user command;
   a. input from panel.
   b. input from positioning mechanism. Set current vector position on display (which could be mid-screen).
6. Start command
   a. start rotation (if rotating transducer is used)
   b. input from positioning mechanism.
      (i) synchronize timing using index pulse
      (ii) activate trigger module
      (iii) fire burst
      (iv) delay onset of acquisition
   c. begin acquisition of ultrasound data (detected/filtered.)
      (i) use sample frequency set by defaults
      (ii) convert new sample and store in display buffer (in the case of vertically displayed vectors)
      (ii-a) use vector number as column address
      (ii-b) use sample number as row address
      (ii-c) continue until sample depth is reached
   d. input from panel (look for stop command)
7. Stop command
   a. stop rotation (if rotating transducer is used)

Figure 20:
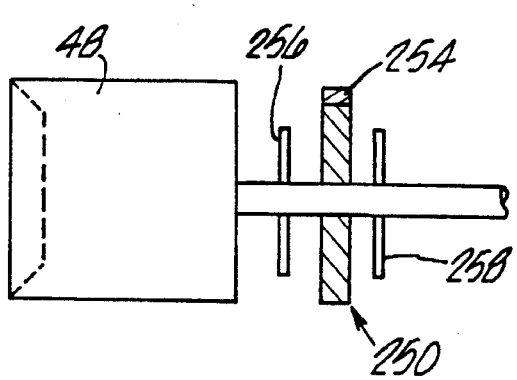
FIG. 20 is a schematically illustrated side-view fragment of a second preferred embodiment of the present invention.
Figure 21:
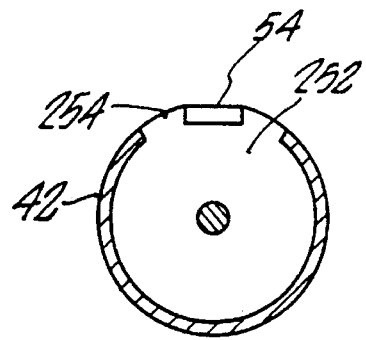
FIG. 21 is a schematically illustrated section view fragment of the FIG. 20 embodiment.

An alternate embodiment of the present catheter is shown in FIGS. 20 and 21. In this embodiment, a separate transducer assembly 250 is positioned behind the cutter 48. The transducer assembly 250 includes a transducer 54 mounted on a transducer support 252. A dovetail 254 on the support 252 locks into the window of the housing. Accordingly, the transducer assembly 250 cannot rotate. Hence, the electrical connections to the transducer are stationary as well and no commutator or inductive coupling is required. A spacer 256 is attached to the drive cable 50 between the back of the cutter and the transducer assembly 250, and a collar 258 is attached to the drive cable 50 on the opposite side of the transducer assembly. The spacer 256 and collar 258 keep the transducer assembly from sliding or shifting longitudinally with respect to the cutter. The transducer assembly can be moved by the window longitudinally and the transducer remains properly oriented or radially aligned with the window. The ringdown effect, if any, can be resolved in the embodiments of FIGS. 20 and 21 by positioning the transducer in a recess on the cutter or the transducer support.

Figure 22:
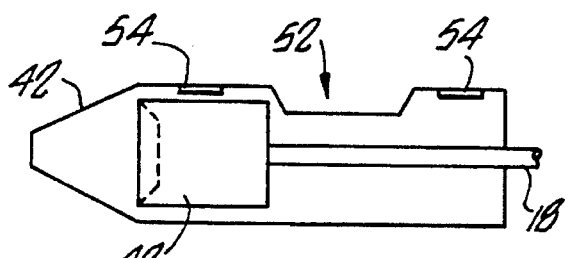
FIG. 22 is a schematically illustrated side view fragment of a third preferred embodiment of the present invention.

In another embodiment, transducers 54 are placed on the housing 42 as shown in FIG. 22. In this embodiment, the entire catheter must be longitudinally moved to obtain a two-dimensional image. Cross-sectional images can be obtained by rotating the entire catheter. Since the balloon 64 cannot be inflated while moving the catheter, no locking is provided. The embodiment of FIG. 22 is therefore more useful in slower moving arteries, such as those in the legs. Arteries in the legs are typically larger in diameter and straighter than other arteries in the body; a more rigid catheter can be used and more easily controlled in leg arteries. Accordingly, with an imaging transducer on the housing outside surface, an image can be created by moving the catheter, instead of moving a carriage or transducer carrier within the catheter.

Figure 23:
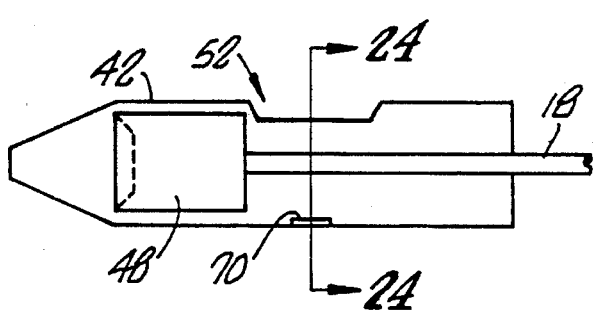
FIG. 23 is a similar view of a fourth preferred embodiment.
Figure 24:
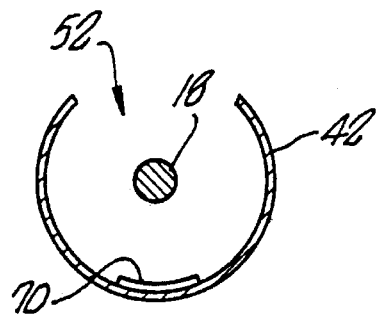
FIG. 24 is a partial section view taken along line 24—24 of FIG. 23.

In yet another embodiment, as shown in FIGS. 23 and 24 a thin film transducer 260 is placed on the inside wall of the housing 42 opposite to the window 52. Imaging is performed when the cutter 48 is moved out of the view of the transducer 260. The field of view of the transducer 260 in this embodiment is relatively narrow. Longitudinal and rotational movement of the catheter can be performed to obtain wider views of the artery.

In the embodiment of FIG. 1, the transducer 42 moves longitudinally with the cutter 48. This movement of the transducer is measured by the encoder from the displacement of the drive cable 50 with respect to the outer wall of the catheter 30. On the other hand, in the embodiments of FIGS. 22–24, since the transducer is attached directly to the catheter housing, movement of the catheter itself must be measured with respect to the patient's body. This is achieved by a catheter movement measuring device (not shown) linked or attached to the catheter and the electronics unit.

Although several embodiments have been shown and described, it will be apparent to those skilled in the art that many modifications and variations can be made thereto without departing from the spirit and scope of the present invention.

What is claimed is:

1. A catheter for ultrasonic imaging within a vessel, said catheter comprising:
   a flexible catheter body;
   a flexible drive cable disposed within the catheter body;
   a transducer housing mounted at the distal end of the catheter body, said transducer housing having a window;
   a rotating device attached to the flexible drive cable;
   a transducer mounted on a component slidably disposed within a region at the distal end of the catheter body during ultrasonic imaging, said transducer being operably connectable to an ultrasonic transmitter, receiver, signal processing unit, and display unit so that said transducer can ultrasonically scan the vessel to create images of the vessel;
   means for longitudinally advancing and retracting the component; and
   means for detecting longitudinal transducer position of the transducer and communicating said transducer position to the signal processing unit for use in constructing an image of the vessel;
   wherein said transducer is held radially stationary while the rotating device is being rotated.

2. The catheter of claim 1, wherein the rotating device is a cutting assembly for atherectomy, said cutting assembly being disposed within the transducer housing so that it can cut material protruding into the transducer housing from without.

3. The catheter of claim 2, wherein the transducer is mounted on a component disposed within the transducer housing during ultrasonic imaging.

4. The catheter of claim 3, wherein the transducer is centered in the window on the transducer housing.

5. The catheter of claim 3, wherein the transducer is mounted on said transducer housing.

6. The catheter of claim 1, wherein the transducer is mounted on a transducer support associated with any one of the rotating device, the transducer housing, or the drive cable.

7. The catheter of claim 6, wherein the transducer support is rotatably connected to the drive cable.

8. The catheter of claim 7, wherein the transducer support is proximally and distally bounded by means for retaining the transducer support at a longitudinal position fixed relative to the longitudinal position of the rotating device.

9. The catheter of claim 1, further comprising means for rapid longitudinal displacement of the transducer relative to the vessel to be imaged.

10. The catheter of claim 9, wherein said means for rapid longitudinal displacement facilitates longitudinal displacement of the transducer relative to the flexible catheter body.

11. The catheter of claim 9, wherein said means for rapid longitudinal displacement comprises a spring attached to a lever arm.

12. A method for ultrasonic imaging within a vessel using a catheter comprising a flexible catheter body, a flexible drive cable disposed within the catheter body, a transducer housing mounted at the distal end of the catheter body, said transducer housing having a window, a transducer mounted on a component disposed within a region at the distal end of the catheter body during ultrasonic imaging, said transducer being operably connectable to an ultrasonic transmitter, receiver, signal processing unit, and display unit so that said transducer can ultrasonically scan the vessel to create images of the vessel, means for longitudinally advancing and retracting the component, and means for detecting longitudinal transducer position of the transducer and communicating said transducer position to the signal processing unit for use in constructing an image of the vessel, said method comprising the steps of:

inserting the flexible catheter body into the vessel to be imaged;

positioning the window on the transducer housing in an area of interest; and generating an image from the transducer by obtaining acoustic information while the transducer is being rapidly displaced longitudinally over a distance greater than five millimeters, said longitudinal displacement occurring relative to said flexible catheter body and, in a time frame small compared to that associated with the heartbeat cycle.

13. The method of claim 12, wherein the longitudinal displacement of the transducer occurs over a period of 0.005 to 1 second.

14. The method of claim 12, wherein the longitudinal displacement of the transducer occurs over a period of 0.005 to 0.3 seconds.

15. The method of claim 12, further comprising the steps of positioning the window on the housing so that material protrudes into the transducer housing from without; and activating a cutting assembly for atherectomy, said cutting assembly being attached to the flexible drive cable and disposed within the transducer housing so that it can cut material protruding into the transducer housing from without.

16. The method of claim 15, wherein the transducer is held radially stationary while the cutting assembly is being rotated.

17. The method of claim 15, wherein the transducer is mounted on a component disposed within the transducer housing during ultrasonic imaging and atherectomy.

18. The method of claim 17, wherein the transducer is mounted on said curing assembly.

19. The method of claim 17, wherein the transducer is mounted on said transducer housing.

20. The method of claim 17, wherein the transducer is mounted on a transducer support associated with any one of the cutting assembly, the transducer housing, or the drive cable.

21. The method of claim 20, wherein the transducer is centered in the window on the transducer housing.

22. The method of claim 21, wherein the transducer support is proximally and distally bound by means for retaining the transducer support at a longitudinal position fixed relative to the longitudinal position of the cutting assembly.

23. The method of claim 20, wherein the transducer support is rotatably connected to the drive cable.

* * * * *